US006406711B1

(12) United States Patent
Lee et al.

(10) Patent No.: US 6,406,711 B1
(45) Date of Patent: Jun. 18, 2002

(54) BONE REGENERATION MATERIAL

(75) Inventors: Jin-Yong Lee, Room No. 1006, Family Apt. 225 Dong, Moonjung 2-dong, Songpa-ku; Hong-Yeoul Kim, 182-7 Donggyo-Dong, Mapo-Gu, both of Seoul (KR); Toshikazu Shiba, Sapporo (JP)

(73) Assignees: Jin-Yong Lee; Hong-Yeoul Kim, both of Seoul (KR)

( * ) Notice: Subject to any disclaimer, the term of this patent is extended or adjusted under 35 U.S.C. 154(b) by 0 days.

(21) Appl. No.: 09/345,389

(22) Filed: Jun. 30, 1999

(30) Foreign Application Priority Data

Jul. 3, 1998 (JP) .............................. 10-204475

(51) Int. Cl.[7] .................................. A61F 2/28
(52) U.S. Cl. ...................... 424/423; 424/424; 424/426
(58) Field of Search ................. 424/422, 423, 424/426, 424, 425

(56) References Cited

U.S. PATENT DOCUMENTS 5,108,755 A    4/1992  Daniels et al. ............. 424/426
5,650,108 A    7/1997  Nies et al. .................. 264/122

FOREIGN PATENT DOCUMENTS

| EP | 0 347 028 A2 | 4/1989 | .......... C01B/25/32 |
| EP | 0 416 761 A1 | 8/1990 | .......... C01B/25/32 |
| EP | 0 555 807 A1 | 9/1993 | .......... A61K/6/097 |
| JP | XP-002122249 | 4/1989 | |
| JP | XP002122248 | 2/1995 | |
| WO | WO 90/12605 | 11/1990 | .......... A61L/27/00 |

OTHER PUBLICATIONS

XP000853507, "Development and characterization of a biodegradable polyphosphate," Journal of Biomedical Materials Research, vol. 34, 95–104 (1997).

Primary Examiner—James M. Spear
(74) Attorney, Agent, or Firm—Jacobson Holman, PLLC

(57) ABSTRACT

A bone regeneration material uses polyphosphoric acid and/or a polyphosphate together with a biocompatible material, a filler for cosmetic surgery, or a bone morphogenetic protein, to expedite new bone formation and shorten healing time or restoration in the treatment of bone fractures or damage.

13 Claims, 7 Drawing Sheets

FIG. 8

BONE REGENERATION MATERIAL

FIELD OF THE INVENTION

The present invention relates to a bone regeneration material for expediting formation of a new bone tissue. More specifically, the invention relates to a bone regeneration material comprising inorganic polyphosphate.

DESCRIPTION OF THE RELATED ART

A bone is a specialized and hardened connective tissue that is composed of cells and an extracellular matrix, and it is different from other connective tissue in that matrix of the bone is mineralized. The mineral is calcium phosphate which is a hydroxyapatite crystal ($Ca_{10}(PO_4)_6(OH)_2$). The bone is an extremely hard tissue capable of providing support and protection from physical stress. Accordingly, the reduction or the damage of the bone owing to the fracture or the pathological to change leads to the disability, the waste of time and money. When the bone is removed by any reasons, the defected bone need to be generated as soon as possible. But if regeneration of the defect cannot occur, replacement of the defect by an artificial bone or by bones from other parts of the body must be operated.

Further, in the treatment of the damage (fracture) of the bone by the physical shock or the damage of the bone accompanied by the surgical operation, the artificial middle setting of various auxiliary bones including artificial bones and immobilization or fixation of fractured portions of bones have been conducted. It takes much time until the bone restores the original shape and function, and the physical and mental stresses of patients are considerably great. Further, the longer the process to healing, the greater the opportunity in which patients might be exposed to bacterial infection. There is a fear that the damaged portions might not be healed completely. Regarding the existing selective materials for increase and regeneration of the bone, various materials which can function as artificial fillers for bone restoration, such as bioceramics, composite materials, bone morphogenetic materials, and natural and synthetic polymers have been studied.

In case of teeth, replacement and reconstruction of fractured, lost, and any pathologically or physiologically wounded bony parts in the oro-maxillofacial region are also important in many aspect. In particular, an alveolar bone supporting the teeth is vulnerable to bacterial infection. Once the alveolar bone is infected or destroyed, it can hardly be restored to the original level by itself. Generally, implantation for constructing an artificial tooth by inserting a metallic implant member in which titanium is used as a base material into a jaw bone is useful with respect to the loss of an inherent tooth. However, this implantation technique is unsatisfactory for supporting the portion of the body around the implanted part, and causes an excess occlusal force to the adjacent bony structure. Thus, this has not always been conducted successfully. As a curing method to solve these problems, there is a method for accelerating regeneration of a tissue and a bone. In order to accelerate regeneration of a bone in a defected bony area, a demineralized bone, hydroxyapatite or the other implant substitute has been used. However, no satisfactory effect has been provided.

For an ideal filler or implant material, properties such as a biocompatibility, a bactericidal activity, a bone morphogenetic activity (stimulus for phenotypically converting mesenchymal cells into osteoblasts in bone formation) and a bone conductive activity (which acts as a lattice for new bone formation) are required. Further, it is advisable that a filler is biodegradable, free from immunogenicity and non-toxic in view of the somatic tissue. However, there is actually no material that meets all of these requirements. Only a material that meets some of these requirements exists.

SUMMARY OF THE INVENTION

It is an object of the invention to provide, for overcoming the defects associated with the conventional bone curing means or substitute bone materials, a bone regeneration material which can expedite new bone formation and shorten a time that lapses until the healing or the restoration.

That is, the invention relates to a bone regeneration material for expediting formation of a new bone tissue, the bone regeneration material containing a linear condensed polyphosphoric acid or/and a polyphosphate. Further, the invention relates to a bone regeneration material for expediting regeneration of a fractured bone wherein a polyphosphate is contained in a substrate composed of a material having a biocompatibility.

Still further, the invention relates to a bone regeneration material for expediting formation of a new bone tissue wherein a polyphosphoric acid is contained in a filler for cosmetic surgery.

Furthermore, the invention relates to a bone regeneration material wherein a polyphosphoric acid is mixed with a bone morphogenetic protein or/and a natural substance containing a bone morphogenetic factor.

DETAILED DESCRIPTION OF THE INVENTION

The polyphosphoric acid includes a linear condensed polyphosphoric acid obtained through dehydrocondensation of an orthophosphoric acid, a side chain polyphosphoric acid in which an organic group is introduced into a side chain, and a cyclic polyphosphoric acid. Especially preferable is a linear condensed polyphosphoric acid represented by formula $(P_nO_{3n+1})_{(n+2)}$ H and having a structure that two or more $PO_4$ tetrahedrons are linearly bound with a top oxygen atom held in common. A polyphosphate is a compound having a molecular structure that hydrogen of a hydroxyl group of a polyphosphoric acid is replaced with a metal. Examples of the metal include sodium and potassium, n is an integer of at least 2, and it is preferably between 5 and 5.000, more preferably between 15 and 2,000. Examples of the substrate composed of the material having the biocompatibility include a synthetic polymer having a biocompatibility, and a sheet, a film, a fiber and a porous material made of a natural material. The polyphosphoric acid is used by being mixed with these materials, by being coated on the surface of the substrate or by being dipped in fibers or a porous material. Examples of the synthetic polymer include non-bioabsorbable polymers such as polypropylene, polyethylene, polyvinyl chloride, polyester, polycarbonate, cellulose, polyamide, polyfluoroethylene and polyurethane; and bioabsorbable polymers such as polyglycolic acid, polylactide, collagen, polyvinyl alcohol, polyvinyl pyrrolidone, polyamino acid, polycaprolactone, polydioxane and a copolymer of vinyl acetate and an unsaturated carboxylic acid. In the bone regeneration material, the polyphosphoric acid is contained in the material having the biocompatibility. The amount of the polyphosphoric acid contained in the material having the biocompatibility is between 0.001 and 20% by weight, preferably between 0.005 and 10% by weight, more preferably between 1 and 5% by weight. When the amount of the polyphosphoric acid exceeds 20% by weight, cells tend to undergo necrosis. When it is less than 0.001% by weight, the effect of the bone regeneration is decreased.

Further, the filler for cosmetic surgery is an artificial bone component used as a bone filler in the cosmetic surgery region. Examples of the filler include hydroxyapatite, calcium secondary phosphate, calcium tertiary phosphate and calcium quaternary phosphate. Examples of the bone morphogenetic protein include bone morphogenetic proteins such as BMP-1, BMP-2 and BMP-3, transforming growth factors such as TGF-b, osteopontin and osteocalcin. Further, examples of the natural substance containing a bone morphogenetic factor include crushed animal bone, mineral-defective bone substrate and the like. The natural substance containing a bone morphogenetic factor is mixed with a polyphosphoric acid in combination with the bone morphogenetic protein, and the mixture can locally be administered as an implant or a device. In this case, the product to be administered is occluded or injected in a physiologically acceptable viscous form free from a pyrogenic substance and suitable for feeding into a fractured bone site. Consequently, a hard or soft bone structure is formed in the fractured bone site, providing a matrix which can be re-absorbed into the body in an optimum state.

The bone regeneration material of the invention is used, as an osterogenic preparation containing the polyphosphoric acid, in the preventive applications such as improvements of the reduction of the occlusive fracture or the complicated fracture and the fixation of artificial joints. Further, the osterogenic preparation newly induces the bone formation, and it is used in the restoration of the innate or traumatic defective portion or the defective portion caused by tumor incision, and in the treatment of the cosmetic surgery, the treatment of the periodontal disease or the other dental restoration process. Moreover, with respect to the bone regeneration material of the invention, the material containing the polyphosphoric acid is used by being coated on the surface of the substrate composed of the material having the biocompatibility, such as a sheet, a film, fibers or a porous material.

The bone regeneration material of the invention can expedite new bone formation and shorten a time that lapses until the healing or the restoration in the treatment of bone fracture owing to a physical shock or of damage of a bone accompanied by surgical operation.

EXAMPLES

The present invention is illustrated specifically by referring to the following Examples.

Example 1

A white rabbit (from New Zealand, body weight 3 kg) was subjected to anesthetic injection, and the thighbone thereof was exposed. Two holes were formed in the neck of the thighbone and near the joint cone, an end of the thighbone using a sterilized drill (3 mm in diameter) until the tip of the drill reached the soft tissue of the thighbone. A collagen tape (CollaTape, supplied by Calcitec) having a size of 1 cm×1 cm was immersed in 30 ml of a 2% sodium polyphosphate (average chain length 75) aqueous solution, and sterilely dried. This collagen tape was embedded in the hole formed in the thighbone on the right leg of the white rabbit. Further, a collagen tape immersed in sterile water as a control was embedded in the hole formed in the thighbone on the left leg of the white rabbit. In this state, the incised portions were sutured, and the conditions of the new bone generation in the holes of the thighbone after 1 and 2 weeks were observed. The thighbones extracted for observation were immobilized with 10% formalin.

Figure 1:
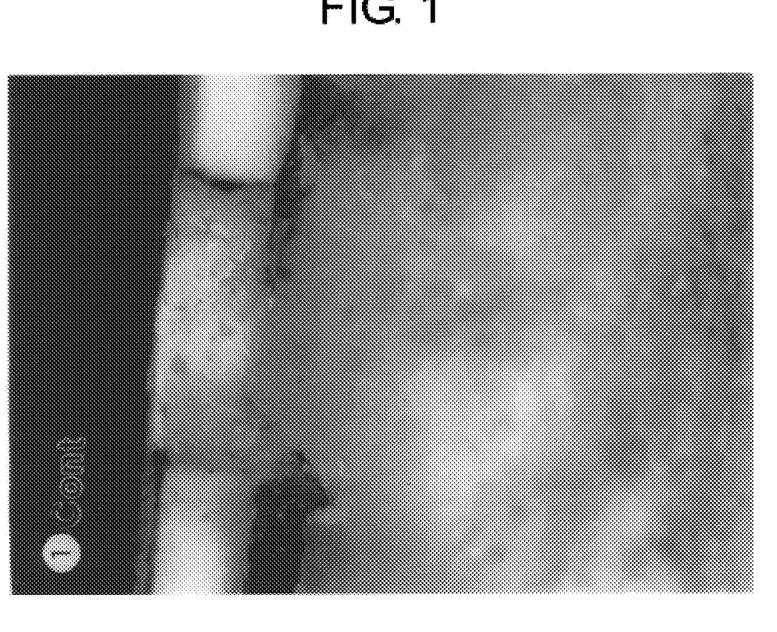
FIG. 1 is a stereoscopic microphotograph of a hole of a thighbone after one week of the treatment with a collagen tape immersed in sterile water.
Figure 2:
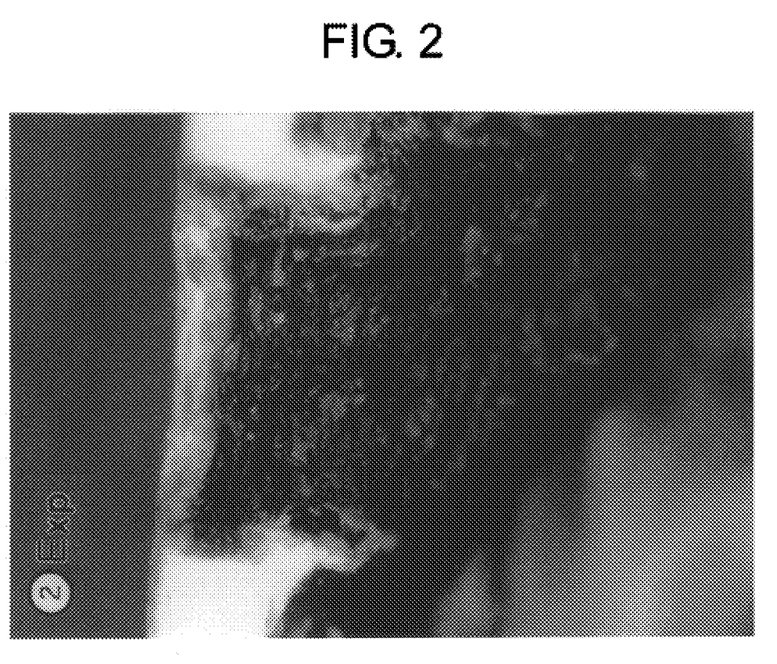
FIG. 2 is a stereoscopic microphotograph of a hole of a thighbone after one week of the treatment with a collagen tape immersed in a polyphosphoric acid aqueous solution.

FIGS. 1 and 2 show states of the holes, after 1 week, which were cut longitudinally, as observed with a stereoscopic microscope. FIG. 1 shows a portion treated with the collagen tape immersed in sterile water. FIG. 2 shows a portion treated with the collagen tape immersed in the polyphosphoric acid aqueous solution. With the collagen tape immersed in sterile water as shown in FIG. 1, no new bone formation was observed at all. Meanwhile, with the collagen tape immersed in the polyphosphoric acid aqueous solution as shown in FIG. 2, it was identified that the new bone in the considerable amount was formed around the bottom edge of the hole, and it was extended to the soft tissue.

A part of the tissue sample in each hole of the thighbone was taken out for histologically observing the state of the new bone formation in the hole of the thighbone after 1 and 2 weeks using the above-mentioned collagen tapes immersed in sterile water and in the polyphosphoric acid aqueous solution. This tissue sample was treated with 10% EDTA for 2 months to conduct decalcification. The sample decalcified was dehydrated with ethanol at various concentrations and finally with xylene, and wrapped in paraffin. The thus-wrapped sample was cut to a thickness of 5 mm, stained with Azan, and observed under a microscope. With respect to the tissue condition after 1 week, the sample treated with the collagen tape immersed in sterile water is shown in FIG. 3, and the sample treated with the collagen tape immersed in the polyphosphoric acid aqueous solution in FIG. 4 respectively.

Figure 3:
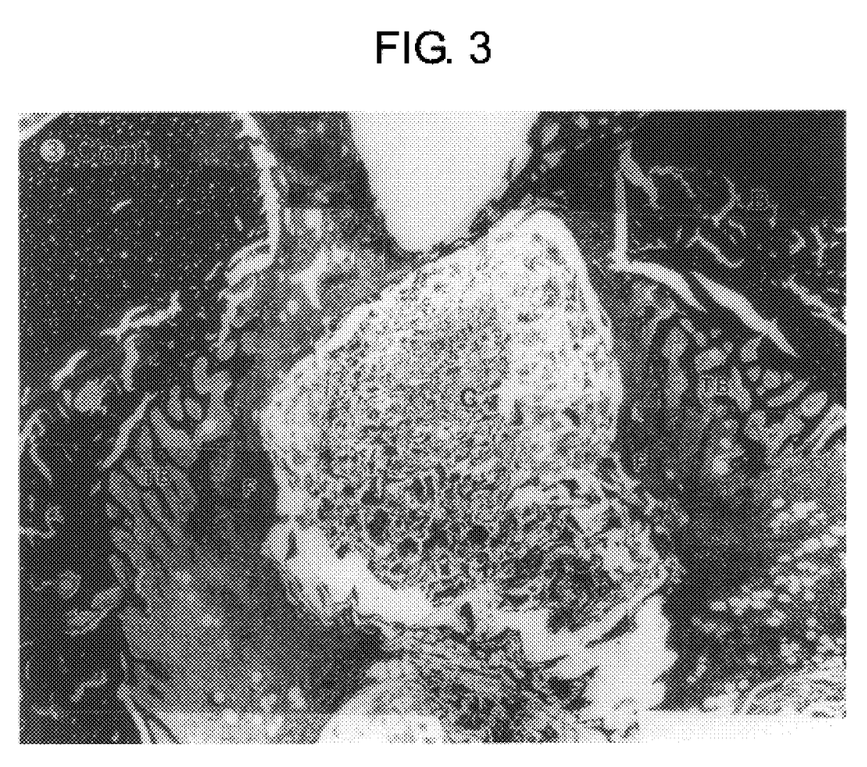
FIG. 3 is a microphotograph of histological observation of a state of new bone formation in a hole of a thighbone after one week of the treatment with a collagen tape immersed in sterile water.
Figure 4:
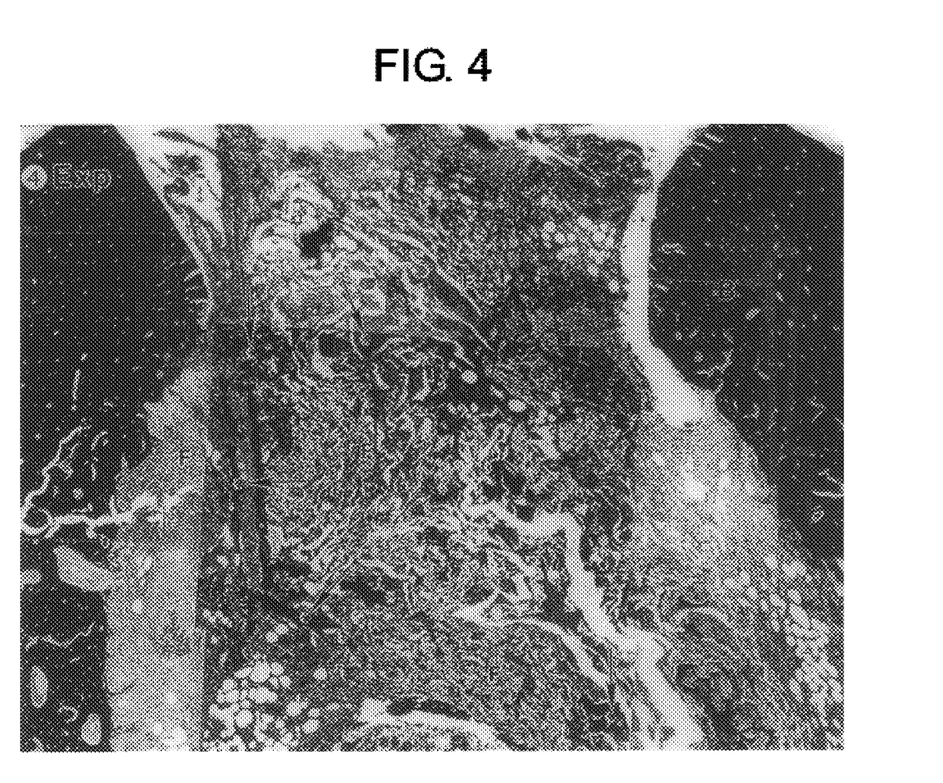
FIG. 4 is a microphotograph of histological observation of a state of new bone formation in a hole of a thighbone after one week of the treatment with a collagen tape immersed in a polyphosphoric acid aqueous solution.

In the sample treated with the collagen tape immersed in sterile water, as is clear from FIG. 3, the collagen tape (C)

was covered with a fibrous tissue (F), and the trabecular bone (TB) derived from the endosteum of the compact bone (B) was approaching to the fibrous tissue. On the other hand, in the sample treated with the collagen tape immersed in the polyphosphoric acid aqueous solution, as shown in FIG. 4, most of the collagen tape was absorbed, and replaced with the fibrous tissue (F). Further, a mass (*) of an immature fibrous trabecular bone derived not from the compact bone (B) but from a new fibrous tissue in the hole could already be identified in six positions of the fibrous tissue.

Figure 5:
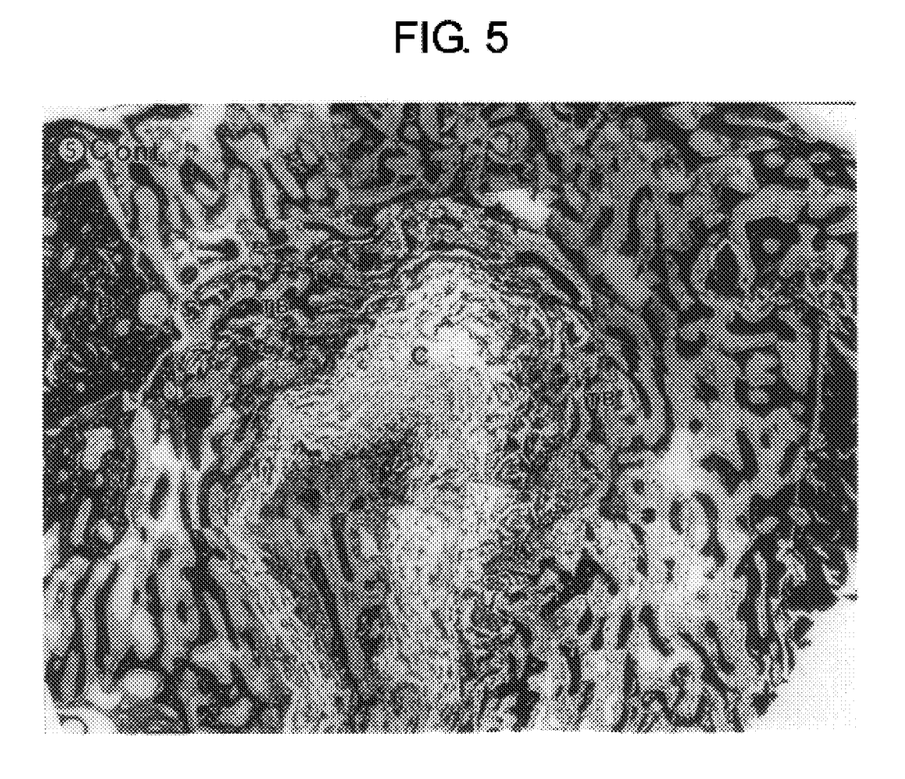
FIG. 5 is a microphotograph of histological observation of a state of new bone formation in a hole of a thighbone after two weeks of the treatment with a collagen tape immersed in sterile water.
Figure 6:
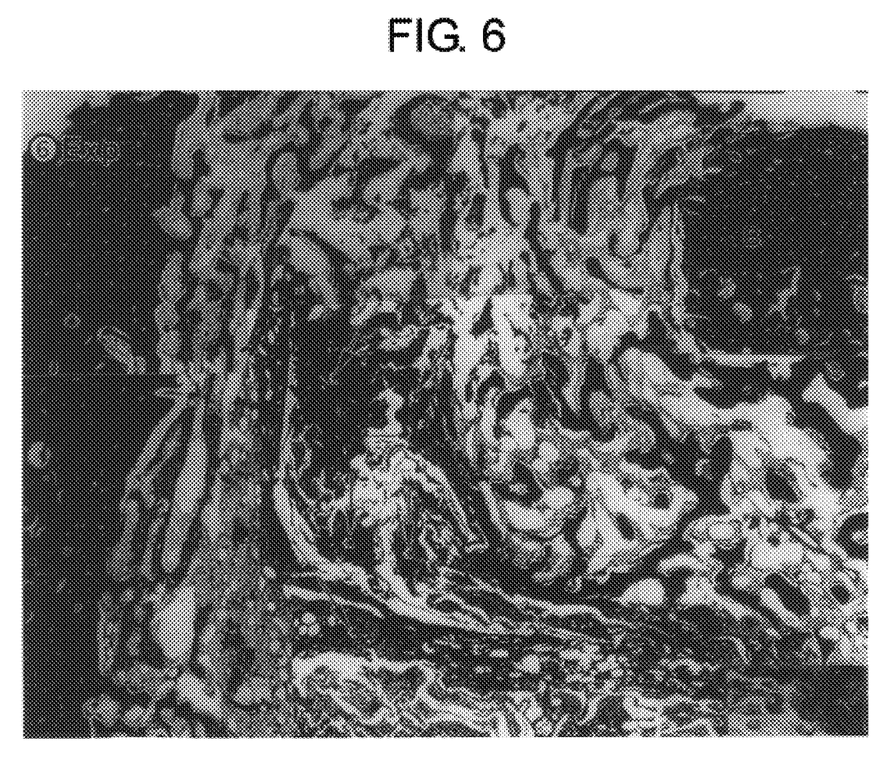
FIG. 6 is a microphotograph of histological observation of a state of new bone formation in a hole of a thighbone after two weeks of the treatment with a collagen tape immersed in a polyphosphoric acid aqueous solution.

Next, with respect to the state after 2 weeks, the sample treated with the collagen tape immersed in sterile water is shown in FIG. 5, and the sample treated with the collagen tape immersed in the polyphosphoric acid aqueous solution in FIG. 6 respectively. In the sample treated with the collagen tape immersed in sterile water, as shown in FIG. 5, both ends of the bone were connected by means of the trabecular bone (TB), but the collagen tape (C) was not completely absorbed, and the trabecular bone (TB) derived from the endosteum surrounded the collagen tape (C) to form a callus. Whereas, the sample treated with the collagen tape immersed in the polyphosphoric acid aqueous solution, as shown in FIG. 6, the collagen tape was absorbed almost completely, and could not be observed. Further, the trabecular bones, primary bones, which were newly formed, were bound to each other, and replaced with the collagen tape. The trabecular bones (*) derived from the new fibrous tissue and replaced with the collagen tape were connected with the trabecular bone derived from the endosteum, and the calluses were formed with the two trabecular bones of the different origins. These restored the holes in such a manner that both ends of the bone were connected therewith.

Example 2

Figure 7:
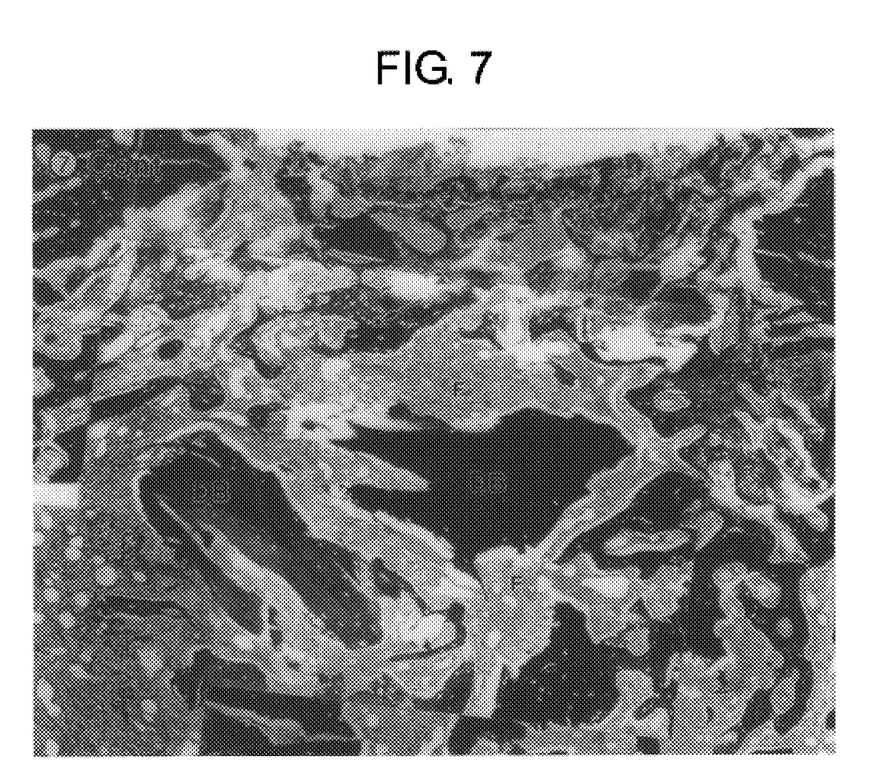
FIG. 7 is a microphotograph of histological observation of a state of new bone formation in a hole of a thighbone after two weeks of the treatment with a dust bone immersed in sterile water.
Figure 8:
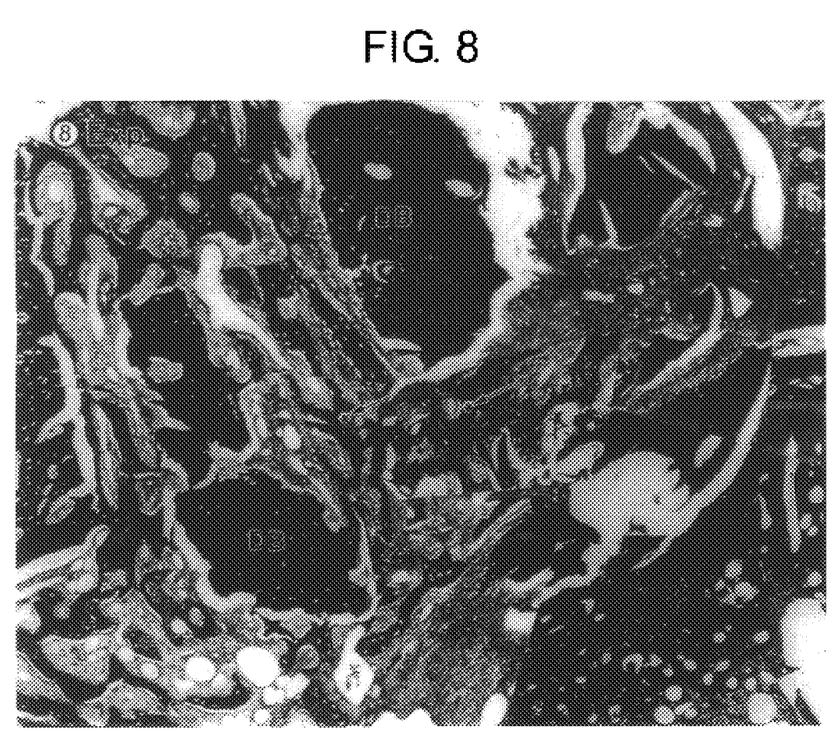
FIG. 8 is a microphotograph of histological observation of a state of new bone formation in a hole of a thighbone after two weeks of the treatment with a dust bone immersed in a polyphosphoric acid aqueous solution.

Holes were formed in the thighbone of the white rabbit in the same manner as in Example 1. Ten milligrams of a human dust bone (particle diameter from 250 to 300 mm) demineralized was immersed in 30 ml of a 2% sodium polyphosphate (average chain length 75) aqueous solution, and sterilely dried. This dust bone was packed in the hole formed in the thighbone on the right leg of the white rabbit. Further, a dust bone immersed in sterile water as a control was packed in the hole formed in the thighbone on the left leg of the white rabbit. In this state, the incised portions were sutured, and the state of the new bone formation in the holes of the thighbone after 2 weeks was histologically observed in the same manner as in Example 1. FIG. 7 shows the results of the electron microscope of the sample treated with the dust bone immersed in sterile water. The hole was mainly filled with the dust bone (DB) and the fibrous tissue (F), and the new trabecular bone was observed only thinly. FIG. 8 shows the results of the electron microscope of the sample treated with the dust bone immersed in the polyphosphoric acid aqueous solution. The hole was filled with the new trabecular bone (*) and the dust bone (DB).

Example 3

Holes were formed in the thighbone of the white rabbit in the same manner as in Example 1. A collagen tape was immersed in 30 ml of a 2% aqueous solution of sodium polyphosphate (Polyphosphate glass, supplied by Sigma) having various chain lengths, and sterilely dried. The collagen tape was embedded in the hole formed in the thighbone on the right leg of the white rabbit. Further, a collagen tape immersed in sterile water as a control was embedded in the hole formed in the thighbone on the left leg of the white rabbit. In this state, the incised portions were sutured, and the state of new bone formation in the holes of the thighbone after 2 weeks was histologically observed. The chain lengths of sodium polyphosphate used were, in terms of the phosphoric acid group. (1) an average chain length of 15 ($Na_{17}P_{15}O_{46}$), (2) an average chain length of 25 ($Na_{27}P_{25}O_{76}$), (3) an average chain length of 35 ($Na_{37}P_{35}O_{106}$) and (4) an average chain length of 65 ($Na_{67}P_{65}O_{196}$).

In the experiments using all of polyphosphoric acids, the new bone formation was accelerated without being influenced with the chain lengths of the polyphosphoric acids.

Example 4

To observe a direct effect of polyphosphate on an osteogenic cell which involves in bone formation, cell activity of MC3T3-EI osteogenic cell originated from a mouse calvarium was determined by MTT(3-[4,5-dimethylthyazol-2-yl]-2,5-diphenyltetrazoium bromide) assay in the presence of polyphosphate with a chain length of 75 at various concentrations.

First, the osteogenic EI cell was grown in $\alpha$-Minimal Essential Medium ($\alpha$-MEM; Gibco, U.S.A.) supplemented with 10% fetal bovine serum(FBS)at 37° C. with 5% $CO_2$. The grown cells were distributed in each well of a 24-well plate, adjusting the cell number to $5\times10^4$ cells per ml and incubated in the same medium for 1 day. The cells were further incubated in the medium without FBS overnight, rip undergoing their Go stage. After removing the cultured medium, the cells were incubated with increasing concentrations (final concentrations of 0.001~0.01%) of polyphosphate in a total of 1 ml of $\alpha$-MEM for 24 hours. Instead of polyphosphate, 10 $\mu$l of distilled water or $\alpha$-MEM with 10% FBS was included in the culture as control. After, discarding the culture supernatant, 450 $\mu$l of $\alpha$-MEM without FBS and 50 $\mu$l of MTT(50 mg/ml: Acros Organics, Belgium) were incubated with the cells for 4 hours at 37° C. with 5% $CO_2$. The supernatant was removed and then the cells treated with 500 $\mu$l of isopropanol containing 0.04N HCl. The resulting mixture was collected and measured its MTT activity colorimetrically at 570 nm as compared at 630 nm as reference.

The MTT activity of MC3T3-EI osteogenic cell at Go stage was increased by approximately 27% in the presence of polyphosphate at the concentrations of 0.001~0.0025%; it was 30% of the increased activity by FBS which contains a variety of growth factors. The activity was gradually decreased down to the control level as concentrations of Polyphosphate increased (Table 1).

TABLE 1

MTT activity of MC3T3-EI osteogenic cell in the presence of polyphosphate with a chain length of 75

| Activators | Absorbance (A570 nm–A630 nm) | Relative percent |
| --- | --- | --- |
| Distilled water | 0.223 | 100.0 |
| Fetal bovines serum (10%) | 0.427 | 191.5 |
| Polyphosphate (0.001%) | 0.282 | 126.5 |
| Polyphosphate (0.0025%) | 0.284 | 127.4 |
| Polyphosphate (0.005%) | 0.260 | 116.6 |
| Polyphosphate (0.0075%) | 0.238 | 106.7 |
| Polyphosphate (0.01%) | 0.222 | 99.6 |

What is claimed is:
1. A method of regenerating bone or expediting formation of new bone which comprises applying to bone a bone-generating composition having a bone generating compo- nent and a biocompatible substrate, wherein the bone generating component is a polyphosphoric acid or a corresponding polyphosphate, and the polyphosphoric acid is a member selected from the group consisting of a) a linear condensed polyphosphoric acid which is a dehydrocondensate of an orthophosphoric acid, b) a side-chain polyphosphoric acid wherein the side chain comprises an organic group, c) a cyclic polyphosphoric acid, and d) a polyphosphoric acid which is a compound of the formula:

$$(P_nO_{3n+1})_{(n+2)}H$$

wherein n is an integer of at least 2, and having a structure wherein two or more $PO_4$ tetrahedrons are linearly bound with a top oxygen atom.

2. A method of claim 1 wherein the polyphosphoric acid is a linear condensed polyphosphoric acid, which is a dehydrocondensate of an orthophosphoric acid.

3. A method of claim 1 wherein the phosphoric acid is a side-chain polyphosphoric acid wherein the side chain comprises an organic group.

4. A method of claim 1 wherein the polyphosphoric acid is a cyclic polyphosphoric acid.

5. A method of claim 1 wherein the polyphosphoric acid is a compound of the formula:

$$(P_nO_{3n+1})_{(n+2)}H$$

wherein n is an integer of at least 2, and having a structure wherein two or more $PO_4$ tetrahedrons are linearly bound with a top oxygen atom.

6. A method of claim 5 wherein n is an integer between 15 and 2,000.

7. A method of regenerating bone or expediting formation of new bone which comprises applying to bone a bone-generating composition which consists essentially of a bone generating component and a biocompatible substrate, wherein the bone generating component is a polyphosphoric acid or a corresponding polyphosphate.

8. A method of claim 7 wherein the bone generating component is in admixture with, coated on or dipped in the substrate, and the substrate is a member selected from the group consisting of a synthetic polymer, a sheet, a film, a fiber, and a porous natural material.

9. A method of claim 8 wherein the synthetic polymer is a bioabsorbable or a non-bioabsorbable polymer.

10. A method of claim 7 wherein the substrate is a member selected from the group consisting of a bone morphogenetic protein and a natural substance containing a bone morphogenetic factor.

11. A method of claim 7 wherein the bone-generating composition comprises from 0.001 to 20 percent by weight of the bone-generating component.

12. A method of claim 7 wherein the composition comprises from 0.001 to 0.01 percent by weight of the polyphosphoric acid and/or the polyphosphate.

13. A method of claim 7 wherein the polyphosphoric acid or the corresponding polyphosphate is water soluble.

* * * * *

UNITED STATES PATENT AND TRADEMARK OFFICE
CERTIFICATE OF CORRECTION

PATENT NO.   : 6,406,711 B1
DATED        : June 18, 2002
INVENTOR(S)  : Jin-Yong Lee et al.

It is certified that error appears in the above-identified patent and that said Letters Patent is hereby corrected as shown below:

Column 3,
Line 5, "$P_nO_{(3n+1)(n+2)}H$" should read -- $P_nO_{(3n+1)}H_{(n+2)}$ --.

Column 7,
Lines 10 and 26, "$P_nO_{(3n+1)(n+2)}H$" should read -- $P_nO_{(3n+1)}H_{(n+2)}$ --.

Signed and Sealed this

Third Day of June, 2003

JAMES E. ROGAN
*Director of the United States Patent and Trademark Office*